United States Patent
Wu et al.

(10) Patent No.: US 10,260,861 B2
(45) Date of Patent: Apr. 16, 2019

(54) OPTICAL MEASURING SYSTEM FOR MAGNIFYING DISPLACEMENT, OPTICAL MEASURING APPARATUS FOR MAGNIFYING DISPLACEMENT AND MEASURING METHOD THEREOF

(71) Applicant: INTAI TECHNOLOGY CORP., Taichung (TW)

(72) Inventors: Shih-Chieh Wu, Taichung (TW); Dian-Ying Lin, Taichung (TW); Chen-Tai Lin, Taichung (TW); Shih-Chang Chuang, Taichung (TW)

(73) Assignee: INTAI TECHNOLOGY CORP., Taichung (TW)

( * ) Notice: Subject to any disclaimer, the term of this patent is extended or adjusted under 35 U.S.C. 154(b) by 0 days.

(21) Appl. No.: 15/785,448

(22) Filed: Oct. 17, 2017

(65) Prior Publication Data
US 2019/0025046 A1 Jan. 24, 2019

(30) Foreign Application Priority Data
Jul. 21, 2017 (CN) .......................... 2017 1 0598582

(51) Int. Cl.
*G01B 11/00* (2006.01)
*G01B 11/08* (2006.01)
(Continued)

(52) U.S. Cl.
CPC .............. *G01B 11/08* (2013.01); *A61B 34/20* (2016.02); *G01B 11/02* (2013.01); *A61B 90/37* (2016.02);
(Continued)

(58) Field of Classification Search
None
See application file for complete search history.

(56) References Cited

U.S. PATENT DOCUMENTS 1,401,119 A * 12/1921 Aldeborgh ............. G01B 5/213
33/501.2
4,193,689 A * 3/1980 Reymond ............... F41G 3/225
356/139.03
(Continued)

FOREIGN PATENT DOCUMENTS

CN 205215354 U 5/2016
TW 201106916 A 3/2011
(Continued)

*Primary Examiner* — Dominic J Bologna
(74) *Attorney, Agent, or Firm* — CKC & Partners Co., LLC

(57) ABSTRACT

An optical measuring apparatus for magnifying displacement includes a seat, a movable abutting member, a plurality of static optical sensing elements and a dynamic optical sensing element. The seat includes a positioning groove. The movable abutting member is pivotally connected to the seat and corresponding to the positioning groove. An object is sandwiched between the movable abutting member and the positioning groove. The static optical sensing elements are disposed on the seat. The dynamic optical sensing element is disposed on the movable abutting member. There is an optical sensing distance between the dynamic optical sensing element and one of the static optical sensing elements. The dynamic optical sensing element is moved along an arc path by the movable abutting member so as to change the optical sensing distance, and a change of the optical sensing distance is greater than a change of a diameter of the object.

16 Claims, 7 Drawing Sheets

(51) Int. Cl.
*G01B 11/02* (2006.01)
*A61B 34/20* (2016.01)
*A61B 90/00* (2016.01)

(52) U.S. Cl.
CPC . *A61B 2034/2055* (2016.02); *A61B 2090/061* (2016.02)

(56) References Cited

U.S. PATENT DOCUMENTS

| | | | | |
|---|---|---|---|---|
| 4,596,076 A | * | 6/1986 | Sigg | G01B 5/08 33/501 |
| 4,893,183 A | * | 1/1990 | Nayar | G06T 7/74 348/135 |
| 6,017,125 A | * | 1/2000 | Vann | G02B 5/122 235/462.32 |
| 6,061,644 A | * | 5/2000 | Leis | G01S 5/163 382/103 |
| 6,147,748 A | * | 11/2000 | Hughes | G01S 7/4812 356/4.09 |
| 6,286,223 B1 | * | 9/2001 | Iwamoto | G01B 5/08 33/555.1 |
| 7,668,584 B2 | * | 2/2010 | Jansen | A61B 34/74 600/424 |
| 7,676,023 B2 | | 3/2010 | Lang | |
| 7,844,105 B2 | * | 11/2010 | Pfister | G06K 9/00208 382/100 |
| 9,007,601 B2 | * | 4/2015 | Steffey | G01B 11/002 356/614 |
| 9,686,532 B2 | * | 6/2017 | Tohme | G01C 15/002 |
| 9,897,428 B2 | * | 2/2018 | Hieb | G01B 5/10 |

FOREIGN PATENT DOCUMENTS

| | | |
|---|---|---|
| TW | 201112997 A | 4/2011 |
| TW | I494536 B | 8/2015 |
| TW | I529368 B | 4/2016 |

* cited by examiner

OPTICAL MEASURING SYSTEM FOR MAGNIFYING DISPLACEMENT, OPTICAL MEASURING APPARATUS FOR MAGNIFYING DISPLACEMENT AND MEASURING METHOD THEREOF

RELATED APPLICATIONS

This application claims priority to China application No. 201710598582.1, filed on Jul. 21, 2017, which is herein incorporated by reference.

BACKGROUND

Technical Field

The present disclosure relates to an optical measuring system, an optical measuring apparatus and an optical measuring method thereof. More particularly, the present disclosure relates to an optical measuring system for magnifying displacement, an optical measuring apparatus for magnifying displacement and an optical measuring method thereof.

Description of Related Art

An optical measuring system, an optical measuring apparatus and an optical measuring method thereof have been widely used in a variety of surgical procedures, such as a neurosurgical procedure, a spinal neurosurgical procedure or other minimally invasive surgical procedures. In general, the optical measuring system, the optical measuring apparatus and the optical measuring method thereof can show the relative positions of a plurality of surgical instruments on a displaying device. Therefore, a physician can obtain the three-dimensional coordinates of the surgical instruments in real time via the optical measuring system, the optical measuring apparatus and the optical measuring method thereof, thereby performing an accurate measurement in the surgical procedure.

One conventional optical measuring apparatus uses the displacement of the optical sensing elements to detect the object and measure the specification of the object. The structure of the conventional optical measuring apparatus can measure different specifications of the surgical instruments or other surgical objects. However, the accuracy of the conventional optical measuring apparatus is not enough to obtain the correct positions when a small difference of the distance is measured, so that there is a deviation between a real position and a virtual position of the surgical object displayed on the displaying device. Moreover, there are many kinds of surgical instruments and surgical objects in the present market, and the specifications of the surgical instruments and the surgical objects are all different (e.g., the diameters or the lengths of the surgical objects are different from each other). Additionally, the conventional optical measuring apparatus is usually made of metal, and has a certain weight and a certain volume. This will increase the difficulty and inconvenience of measurement in the surgical procedure and an operating burden on the physician. Therefore, an optical measuring system, an optical measuring apparatus and an optical measuring method thereof which are simple in operation and capable of precisely measuring the diameter and length of the object are commercially desirable.

SUMMARY

According to one aspect of the present disclosure, an optical measuring apparatus for magnifying displacement to measure a diameter of an object includes a seat, a movable abutting member, a plurality of static optical sensing elements and a dynamic optical sensing element. The seat includes a positioning groove. The movable abutting member is pivotally connected to the seat and corresponding to the positioning groove. The object is sandwiched between the movable abutting member and the positioning groove. The static optical sensing elements are disposed on the seat. The dynamic optical sensing element is disposed on the movable abutting member. There is an optical sensing distance between the dynamic optical sensing element and one of the static optical sensing elements. The dynamic optical sensing element is moved along an arc path by the movable abutting member so as to change the optical sensing distance, and a change of the optical sensing distance is greater than a change of the diameter of the object.

According to another aspect of the present disclosure, an optical measuring system for magnifying displacement to measure a diameter and a length of an object includes an optical measuring apparatus for magnifying displacement, an optical tracker and an axial optical measuring device. The optical measuring apparatus for magnifying displacement includes a seat, a movable abutting member, a plurality of static optical sensing elements and a dynamic optical sensing element. The seat includes a positioning groove. The movable abutting member is pivotally connected to the seat and corresponding to the positioning groove. The object is sandwiched between the movable abutting member and the positioning groove. The static optical sensing elements are disposed on the seat. The dynamic optical sensing element is disposed on the movable abutting member. There is an optical sensing distance between the dynamic optical sensing element and one of the static optical sensing elements. The dynamic optical sensing element is moved along an arc path by the movable abutting member so as to change the optical sensing distance, and a change of the optical sensing distance is greater than a change of the diameter of the object. The optical tracker is oriented towards the static optical sensing elements and the dynamic optical sensing element to detect the static optical sensing elements and the dynamic optical sensing element so as to identify the diameter of the object. The axial optical measuring device includes a gripping body and an optical sensor. The gripping body is detachably connected to the object. The optical sensor is disposed on the gripping body. The optical sensor is detected by the optical tracker to identify the length of the object.

According to further another aspect of the present disclosure, a measuring method applied to the optical measuring apparatus for magnifying displacement provides an object disposing step and a radial optical detecting step. The object disposing step is for disposing the object between the movable abutting member and the positioning groove so as to tightly connect the object between the movable abutting member and the positioning groove. The radial optical detecting step is for driving an optical tracker to detect the static optical sensing elements and the dynamic optical sensing element so as to identify the diameter of the object.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
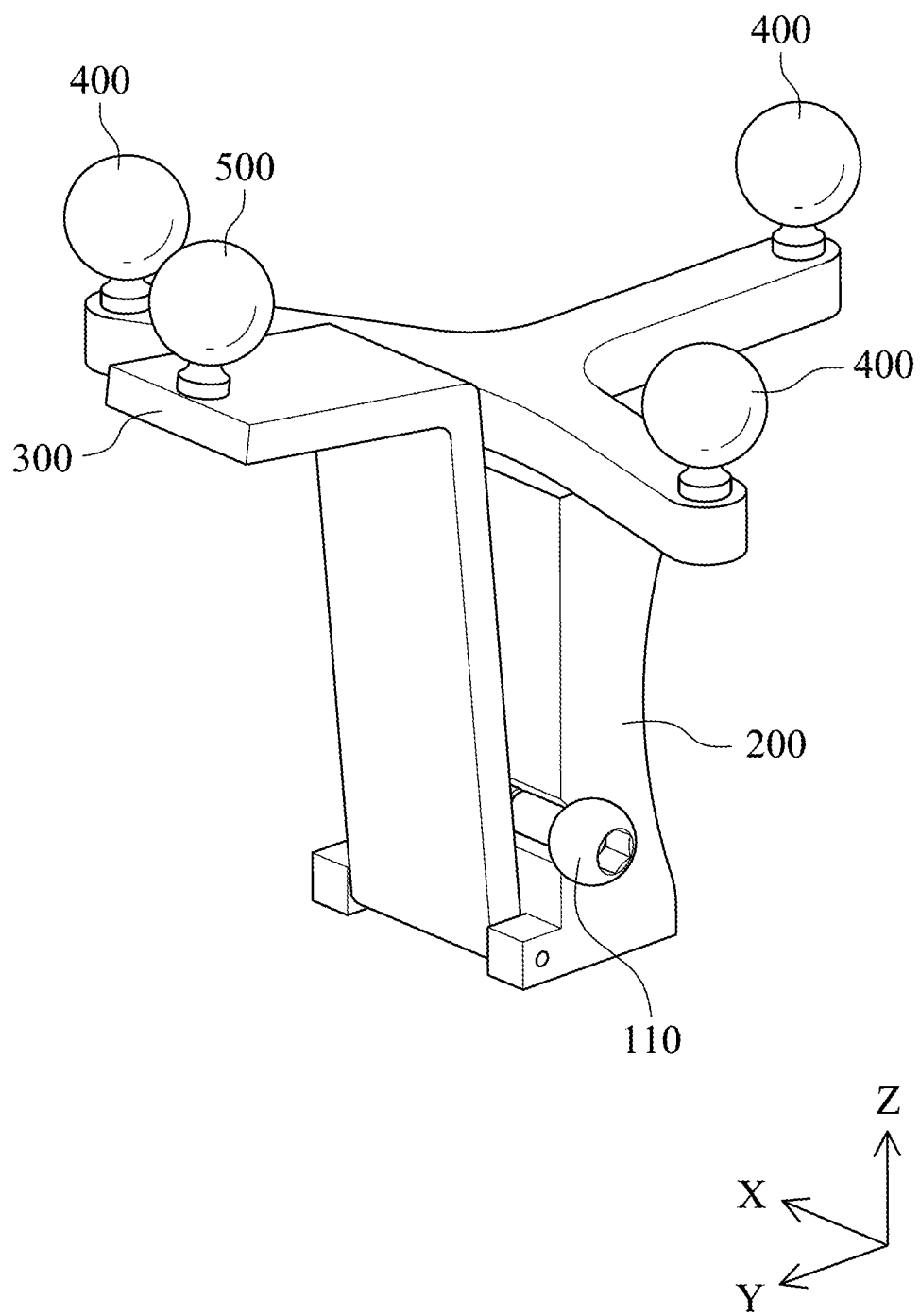
FIG. 1 shows a schematic view of an optical measuring apparatus for magnifying displacement according to one embodiment of the present disclosure.
Figure 2:
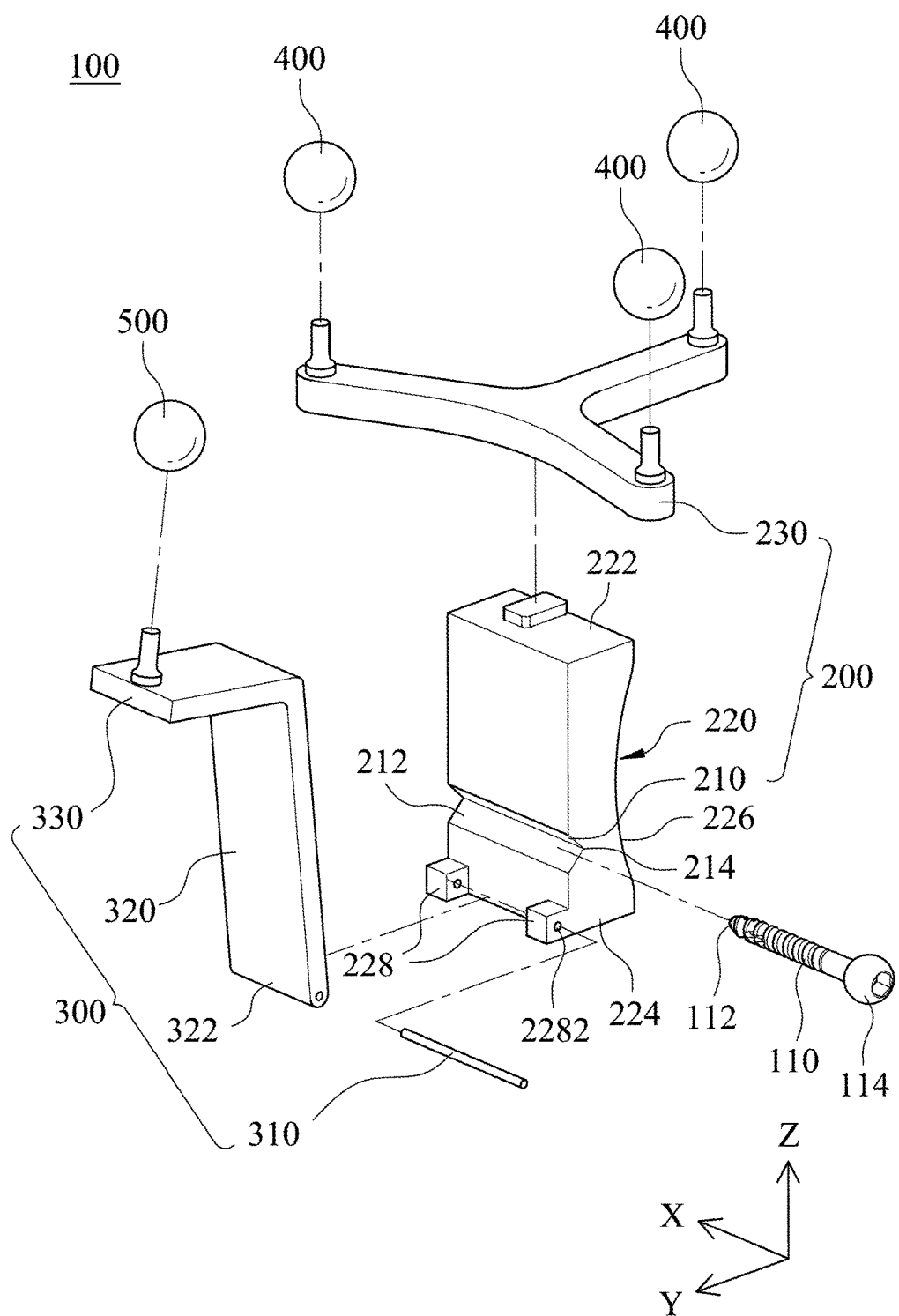
FIG. 2 shows an exploded view of the optical measuring apparatus for magnifying displacement of FIG. 1.
Figure 3A:
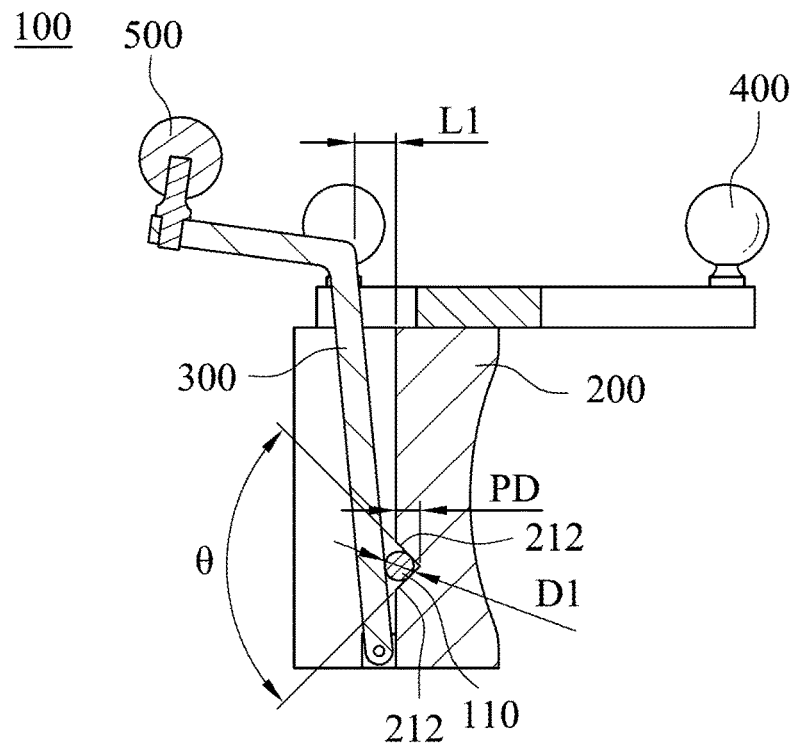
FIG. 3A shows a cross-sectional view of the optical measuring apparatus for magnifying displacement to measure a diameter of one object of FIG. 1.
Figure 3B:
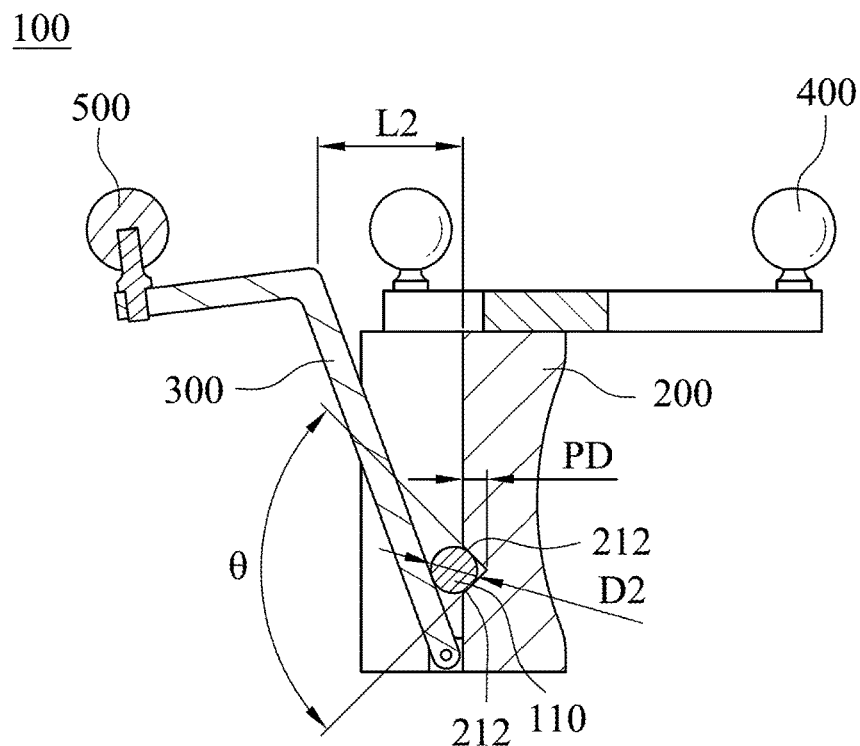
FIG. 3B shows a cross-sectional view of the optical measuring apparatus for magnifying displacement to measure a diameter of another object of FIG. 1.

FIG. 1 shows a schematic view of an optical measuring apparatus 100 for magnifying displacement according to one embodiment of the present disclosure; FIG. 2 shows an exploded view of the optical measuring apparatus 100 for magnifying displacement of FIG. 1; FIG. 3A shows a cross-sectional view of the optical measuring apparatus 100 for magnifying displacement to measure a diameter of one object 110 of FIG. 1; and FIG. 3B shows a cross-sectional view of the optical measuring apparatus 100 for magnifying displacement to measure a diameter of another object 110 of FIG. 1. The optical measuring apparatus 100 for magnifying displacement is used to measure the diameter of the object 110. The optical measuring apparatus 100 for magnifying displacement includes a seat 200, a movable abutting member 300, three static optical sensing elements 400 and a dynamic optical sensing element 500.

The seat 200 is used for positioning the object 110 and allowing an operator to hold. In detail, the seat 200 includes a positioning groove 210, a seat body 220 and a dynamic reference frame 230 (DRF). The positioning groove 210 includes two abutting inclined surfaces 212. The two abutting inclined surfaces 212 are formed into a V-shape and intersect each other at an intersection 214. The object 110 is spaced from the intersection 214 by an intersecting distance. The positioning groove 210 has a positioning depth PD, and the positioning depth PD is smaller than a sum of the diameter and the intersecting distance. In FIG. 2, the object 110 is a bone screw having a cylindrical shape. The diameter of the bone screw (i.e., the object 110) is about 4-8 mm. In addition, there is an angle θ between the two abutting inclined surfaces 212, and the angle θ is greater than or equal to 80 degrees and smaller than or equal to 100 degrees. In FIGS. 3A and 3B, the angle θ is 90 degrees. The V-shape structure of the two abutting inclined surfaces 212 allows the object 110 having a circular shape, an arc shape or a rectangular shape to position on the positioning groove 210. Moreover, the seat 220 includes a top end 222, a bottom end 224 and a supporting surface 226. The positioning groove 210 is concavely disposed on the seat body 220. The top end 222 is connected to the dynamic reference frame 230. The bottom end 224 is pivotally connected to the movable abutting member 300. The supporting surface 226 has an arc shape and is corresponding to the positioning groove 210, and the supporting surface 226 is located between the top end 222 and the bottom end 224. The bottom end 224 of the seat body 220 includes two convex lugs 228, and each of the two convex lugs 228 has a hole 2282. The two convex lugs 228 are configured to pivotally connect the seat 200 to the movable abutting member 300. The dynamic reference frame 230 has three light ball positioning terminals. The three static optical sensing elements 400 are positioned on the three light ball positioning terminals, respectively.

The movable abutting member 300 is pivotally connected to the seat 200 and corresponding to the positioning groove 210. The object 110 is sandwiched between the movable abutting member 300 and the positioning groove 210. In detail, the movable abutting member 300 includes a shaft 310, a pivotal portion 320 and a light ball positioning portion 330. The shaft 310 is disposed through the two holes 2282 of the two convex lugs 228. The pivotal portion 320 is pivotally connected to the shaft 310. The shaft 310 is communicated between the two convex lugs 228 and a pivot connecting terminal 322 of the pivotal portion 320. The light ball positioning portion 330 is integrally connected to the pivotal portion 320. The dynamic optical sensing element 500 is positioned on the light ball positioning portion 330. Moreover, the top end 222 of the seat 200 is spaced from the movable abutting member 300 by an opening distance. The rotation of the movable abutting member 300 affects the size of the opening distance.

The three static optical sensing elements 400 are disposed on the seat 200. In detail, the three static optical sensing elements 400 are respectively positioned on the three light ball positioning terminals disposed on the dynamic reference frame 230. In other words, the three static optical sensing elements 400 are connected to the dynamic reference frame 230 via the three light ball positioning terminals. In FIGS. 1-3B, the static optical sensing elements 400 and the dynamic optical sensing element 500 are reflective balls. According to the reflective balls, the optical tracker 700 can instantly identify and track the precise positions of the static optical sensing elements 400 and the dynamic optical sensing element 500. Certainly, the number of the static optical sensing elements 400 may be changed to meet the different needs of various applications, such as four static optical sensing elements 400.

The dynamic optical sensing element 500 is disposed on the movable abutting member 300. There is an optical sensing distance between the dynamic optical sensing element 500 and one of the three static optical sensing elements 400. The dynamic optical sensing element 500 is moved along an arc path by the movable abutting member 300 so as to change the optical sensing distance. In other words, the arc path of the dynamic optical sensing element 500 is a partial circular trajectory according to the shaft 310 as a central axis, so that the dynamic optical sensing element 500 is rotated around the shaft 310. When the dynamic optical sensing element 500 is moved with the movable abutting member 300, a linear distance between the dynamic optical sensing element 500 and each of the three static optical sensing elements 400 is changed based on the movement of the dynamic optical sensing element 500. In addition, a change of the optical sensing distance is greater than a change of the diameter of the object 110. A change of the opening distance is greater than the change of the diameter of the object 110. For example, when the diameter of the object 110 is equal to a first diameter D1, and the object 110 is tightly clamped between the positioning groove 210 of the seat 200 and the movable abutting member 300, the opening distance is equal to a first spacing value L1, as shown in FIG. 3A. When the diameter of the object 110 is equal to a second diameter D2, and the object 110 is tightly clamped between the positioning groove 210 of the seat 200 and the movable abutting member 300, the opening distance is equal to a second spacing value L2, as shown in FIG. 3B. The second diameter D2 is greater than the first diameter D1. The second spacing value L2 is greater than the first spacing value L1. The value of "L2−L1" is greater than the value of "D2−D1", and the above feature represents "magnifying displacement" of the present disclosure. There is an acute angle between the movable abutting member 300 and the seat 200. The acute angle is positively correlated with the opening distance. The larger the acute angle is, the larger the opening distance is. Conversely, the smaller the acute angle is, the smaller the opening distance is. Accordingly, the optical measuring apparatus 100 for magnifying displacement of the present disclosure utilizes arc movements of the movable abutting member 300 and the dynamic optical sensing element 500 to magnify the change of diameter of the object 110 so as to improve the accuracy of measurements. Moreover, due to the simple structure, it is convenient for operation and very suitable for the measurement of surgical instruments. The optical measuring apparatus 100 for magnifying displacement of the present disclosure can be made of a medical material, so that the hardness of the optical measuring apparatus 100 is much lower than the hardness of a conventional metal optical measuring apparatus. A weight and a volume of the optical measuring apparatus 100 are both smaller than the weight and the volume of the conventional metal optical measuring apparatus, thereby significantly reducing an operating burden on a physician.

Figure 4:
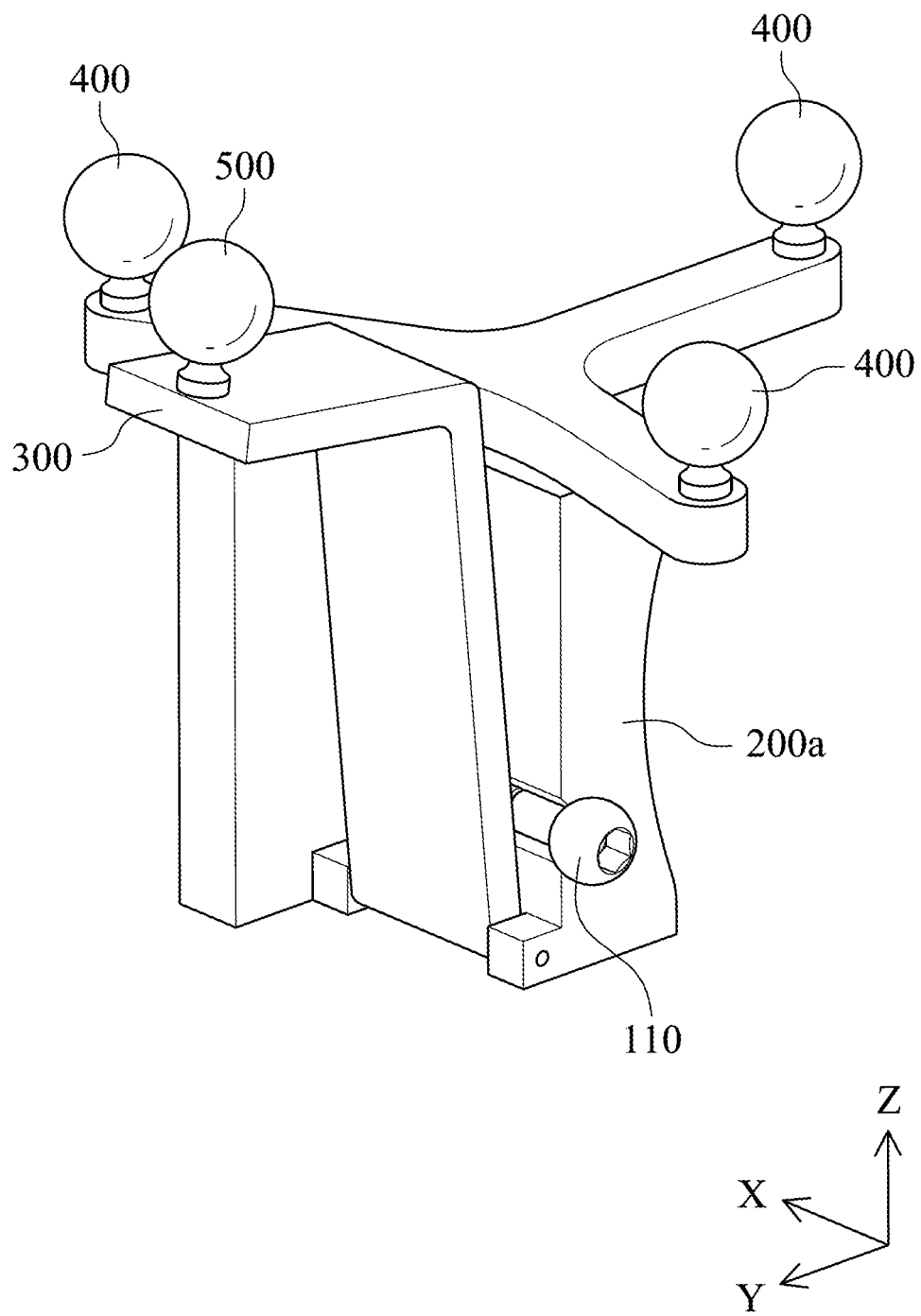
FIG. 4 shows a schematic view of an optical measuring apparatus for magnifying displacement according to another embodiment of the present disclosure.
Figure 5:
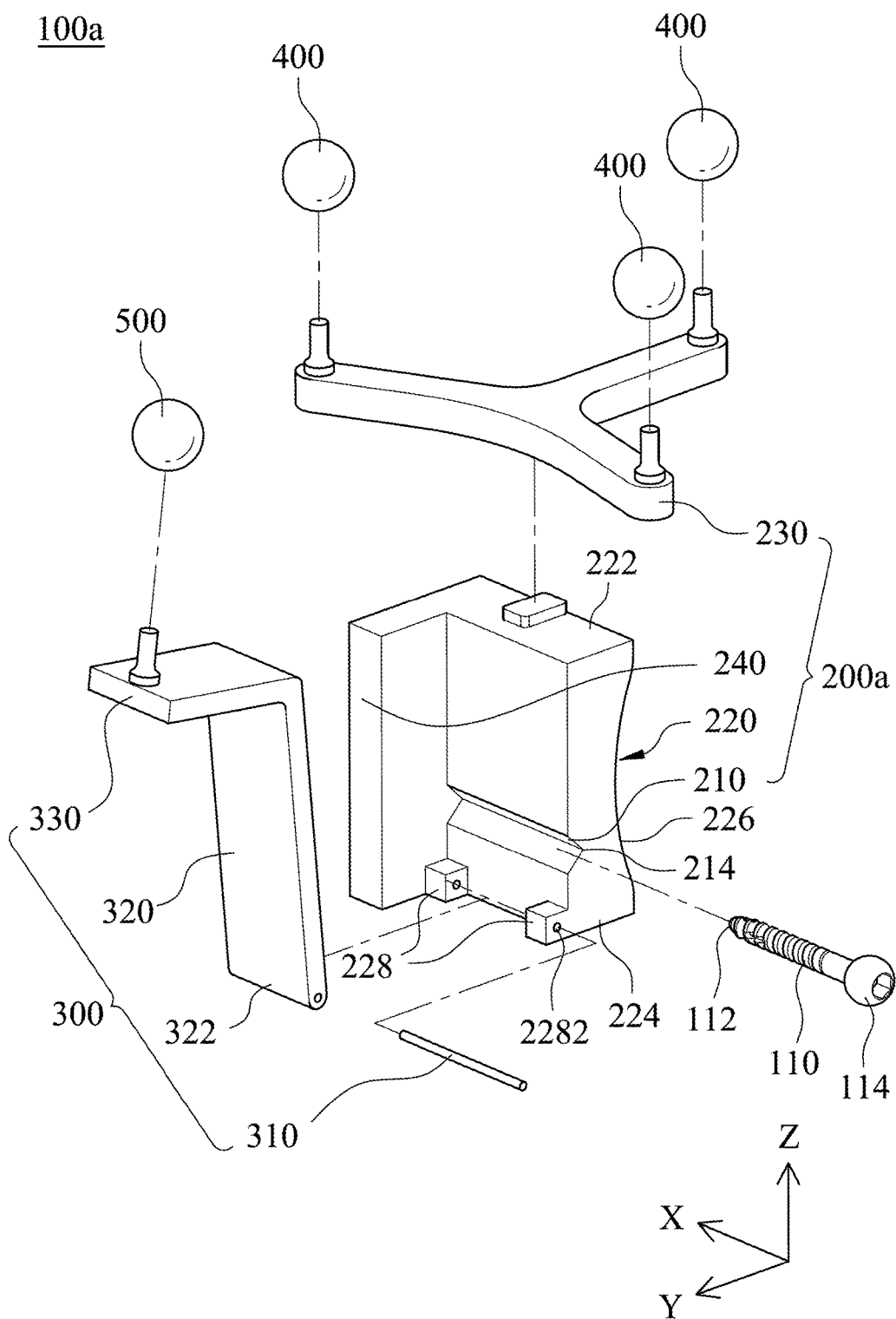
FIG. 5 shows an exploded view of the optical measuring apparatus for magnifying displacement of FIG. 4.

FIG. 4 shows a schematic view of an optical measuring apparatus 100a for magnifying displacement according to another embodiment of the present disclosure; and FIG. 5 shows an exploded view of the optical measuring apparatus 100a for magnifying displacement of FIG. 4. The optical measuring apparatus 100a for magnifying displacement includes a seat 200a, a movable abutting member 300, three static optical sensing elements 400 and a dynamic optical sensing element 500.

In FIGS. 4 and 5, the detail of the movable abutting member 300, the three static optical sensing elements 400 and the dynamic optical sensing element 500 are the same as the embodiment of FIG. 2. In FIGS. 4 and 5, the optical measuring apparatus 100a further includes the seat 200a. The seat 200a includes a positioning groove 210, a seat body 220, a dynamic reference frame 230 and a blocking member 240. The difference between the seat 200a of FIG. 5 and the seat 200 of FIG. 2 is that the blocking member 240 is convexly disposed on the seat body 220 and connected to the positioning groove 210. The blocking member 240 blocks one end of the positioning groove 210. When the object 110 is placed in the positioning groove 210, the blocking member 240 is abutted against a front end 112 of the object 110 so as to prevent the object 110 from moving in an extending direction of the positioning groove 210. The extending direction of the positioning groove 210 is parallel to an X-axis direction. In FIGS. 4 and 5, the blocking member 240 is integrally connected to the seat body 220. The object 110 is the bone screw having the cylindrical shape. The front end 112 of the object 110 is positioned by the blocking member 240 to avoid sliding motion of the object 110 while measuring the object 110, thus increasing the convenience and efficiency of the measuring operation.

Figure 6:
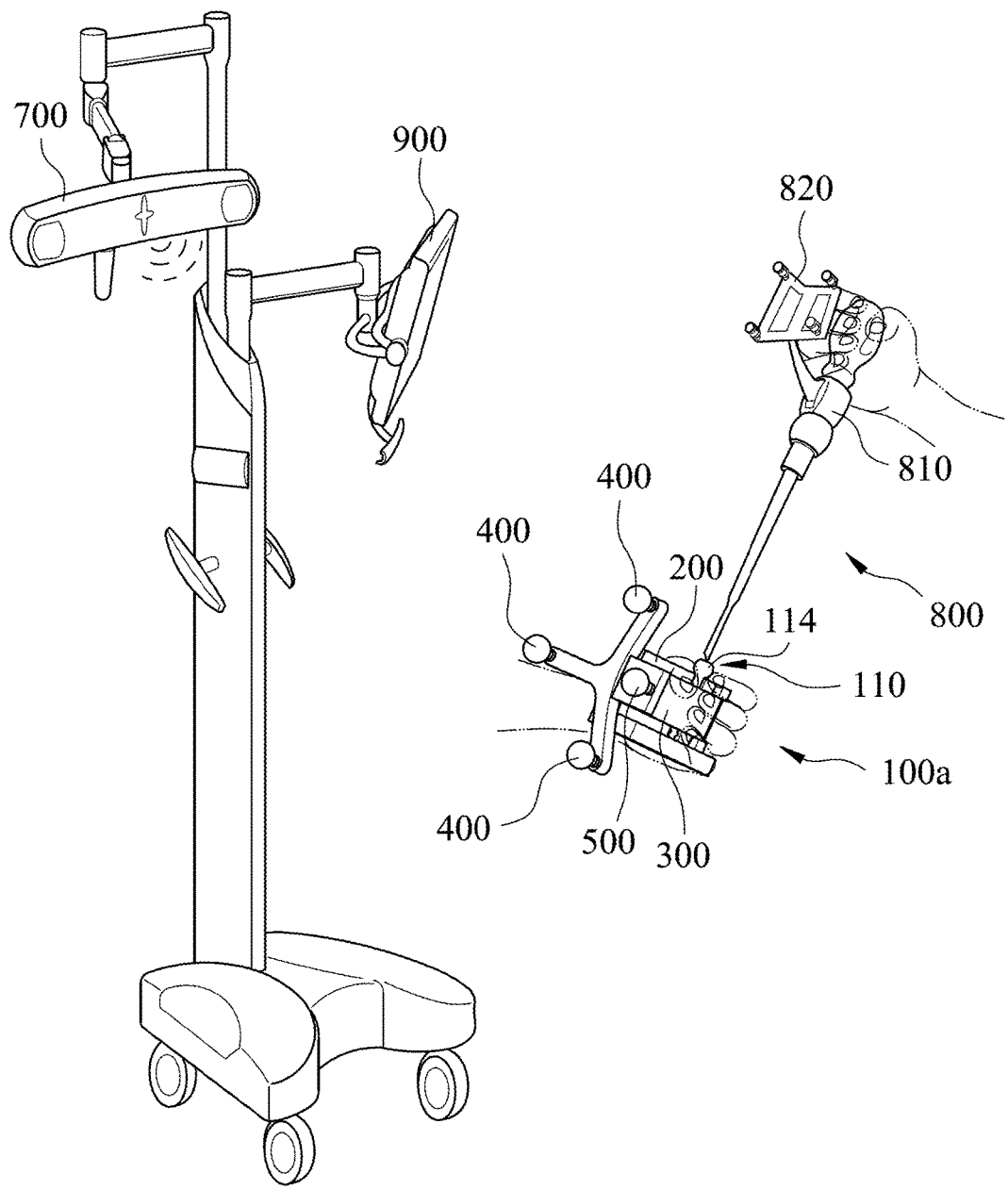
FIG. 6 shows a schematic view of an optical measuring system for magnifying displacement according to one embodiment of the present disclosure.

FIG. 6 shows a schematic view of an optical measuring system 600 for magnifying displacement according to one embodiment of the present disclosure. The optical measuring system 600 for magnifying displacement is configured to measure a diameter and a length of an object 110. The optical measuring system 600 for magnifying displacement includes an optical measuring apparatus 100a, an optical tracker 700, an axial optical measuring device 800 and a displaying device 900.

In FIG. 6, the detail of the optical measuring apparatus 100a is the same as the embodiment of FIG. 5. The optical tracker 700 is oriented towards the static optical sensing elements 400 and the dynamic optical sensing element 500 to detect the static optical sensing elements 400 and the dynamic optical sensing element 500 so as to identify the diameter of the object 110. The axial optical measuring device 800 includes a gripping body 810 and an optical sensor 820. The gripping body 810 is detachably connected to a rear end 114 of the object 110. The optical sensor 820 is disposed on the gripping body 810. In detail, the optical sensor 820 includes four axial optical sensing elements and an axial dynamic reference frame. The four axial optical sensing elements are positioned on the axial dynamic reference frame. The axial dynamic reference frame is connected between the four axial optical sensing elements and the gripping body 810. The optical sensor 820 is detected by the optical tracker 700 to identify the length of the object 110. The optical sensor 820 combined with the static optical sensing elements 400 and the dynamic optical sensing element 500 of the optical measuring apparatus 100a can detect precise positions of the front end 112 and the rear end 114 of the object 110, thereby accurately identifying the length of the object 110. The displaying device 900 is signally connected to the optical tracker 700 to visually display the length and the diameter of the object 110 to the operator (i.e., the physician). In addition, in the procedure for measuring the object 110, the operator holds the axial optical measuring device 800 with one hand and the optical measuring apparatus 100a with the other hand. The other hand of the operator may touch the supporting surface 226, the blocking member 240 and/or the movable abutting member 300. Then, the four axial optical sensing elements of the optical sensor 820, the three static optical sensing elements 400 and the dynamic optical sensing element 500 of the optical measuring apparatus 100a are simultaneously oriented towards the optical tracker 700 by the operator to track the position of the object 110 and obtain the correct length of the object 110. Therefore, the optical measuring system 600 for magnifying displacement of the present disclosure can not only measure the diameter of the object 110, but also measure the length of the object 110 so as to be convenient for the physician and reduce the operating burden.

Figure 7:
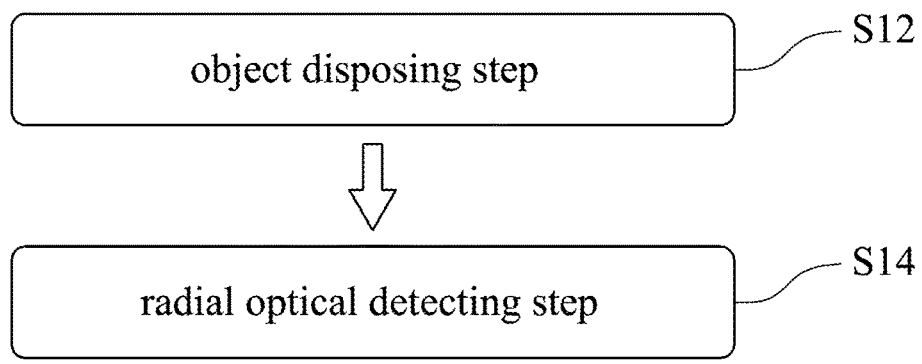
FIG. 7 shows a flow chart of a measuring method applied to an optical measuring apparatus for magnifying displacement according to one embodiment of the present disclosure.

FIG. 7 shows a flow chart of a measuring method 1000 applied to an optical measuring apparatus 100, 100a for magnifying displacement according to one embodiment of the present disclosure. In FIGS. 1, 2, 4, 5 and 7, the measuring method 1000 cooperated with the optical measuring apparatus 100 or the optical measuring apparatus 100a is used to measure the diameter of the object 110. The measuring method 1000 provides an object disposing step S12 and a radial optical detecting step S14. The object disposing step S12 is for disposing the object 110 between the movable abutting member 300 and the positioning groove 210 and applying external forces to the movable abutting member 300 and the positioning groove 210 so as to tightly connect the object 110 between the movable abutting member 300 and the positioning groove 210. The object 110 is tightly clamped between the movable abutting member 300 and the positioning groove 210. Additionally, the radial optical detecting step S14 is for driving the optical tracker 700 to detect the positions of the static optical sensing elements 400 and the dynamic optical sensing element 500 so as to identify the diameter of the object 110. Hence, the measuring method 1000 of the present disclosure can accurately measure the diameter of the object 110 by a simple structure and an easy operation of the optical measuring apparatus 100 or the optical measuring apparatus 100a. Furthermore, the measuring method 1000 of the present disclosure utilizes arc movements of the movable abutting member 300 and the dynamic optical sensing element 500 to magnify the change of diameter of the object 110 so as to greatly improve the accuracy of measurements.

Figure 8:
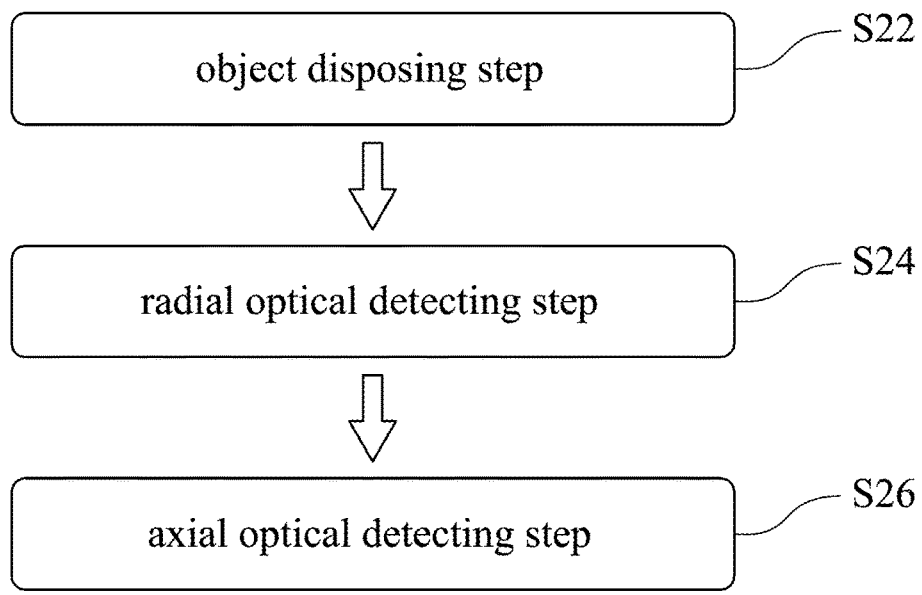
FIG. 8 shows a flow chart of a measuring method applied to an optical measuring apparatus for magnifying displacement according to another embodiment of the present disclosure.

FIG. 8 shows a flow chart of a measuring method 1000a applied to an optical measuring apparatus 100a for magnifying displacement according to another embodiment of the present disclosure. In FIGS. 5, 6 and 8, the measuring method 1000a is utilized to measure the diameter and the length of the object 110, and can be applied to an optical measuring system 600. The measuring method 1000a provides an object disposing step S22, a radial optical detecting step S24 and an axial optical detecting step S26. The detail of the object disposing step S22 and the radial optical detecting step S24 are the same as the embodiment of FIG. 7. The axial optical detecting step S26 is for driving the optical tracker 700 to detect an optical sensor 820 of an axial optical measuring device 800 so as to identify the length of the object 110. The steps of the measuring method 1000a are carried out in order of the object disposing step S22, the radial optical detecting step S24 and the axial optical detecting step S26. Accordingly, the measuring method 1000a of the present disclosure uses the optical measuring apparatus 100a cooperated with the axial optical measuring device 800 to enable the physician to precisely measure the diameter and the length of the object 110. Additionally, because of the simple operation and the lightweight apparatus, it is greatly suitable for use by the physician.

According to the aforementioned embodiments and examples, the advantages of the present disclosure are described as follows.

1. The optical measuring apparatus for magnifying displacement of the present disclosure utilizes arc movements of the movable abutting member and the dynamic optical sensing element to magnify the change of diameter of the object so as to improve the accuracy of measurements.

2. Due to the simple structure of the optical measuring apparatus for magnifying displacement of the present disclosure, it is convenient for operation and very suitable for the measurement of surgical instruments.

3. The optical measuring system for magnifying displacement of the present disclosure can not only measure the diameter of the object, but also measure the length of the object so as to be convenient for the physician and reduce the operating burden.

4. The optical measuring apparatus for magnifying displacement of the present disclosure can be made of a medical material, so that a weight and a volume of the optical measuring apparatus are both smaller than the weight and the volume of the conventional metal optical measuring apparatus, thereby significantly reducing an operating burden on the physician.

5. The front end of the object can be positioned by the blocking member of the present disclosure to avoid sliding motion of the object while measuring the object, thus increasing the convenience and efficiency of the measuring operation.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An optical measuring apparatus for magnifying displacement to measure a diameter of an object, the optical measuring apparatus for magnifying displacement comprising:
    a seat comprising a positioning groove;
    a movable abutting member pivotally connected to the seat and corresponding to the positioning groove, wherein the object is sandwiched between the movable abutting member and the positioning groove;
    a plurality of static optical sensing elements disposed on the seat; and
    a dynamic optical sensing element disposed on the movable abutting member, wherein there is an optical sensing distance between the dynamic optical sensing element and one of the static optical sensing elements, the dynamic optical sensing element is moved along an arc path by the movable abutting member so as to change the optical sensing distance, and a change of the optical sensing distance is greater than a change of the diameter of the object.

2. The optical measuring apparatus for magnifying displacement of claim 1, wherein the seat further comprises:
    a seat body having a top end and a bottom end, wherein the positioning groove is concavely disposed on the seat body, and the bottom end is pivotally connected to the movable abutting member; and
    a dynamic reference frame connected to the top end and having a plurality of light ball positioning terminals, wherein the static optical sensing elements are positioned on the light ball positioning terminals, respectively.

3. The optical measuring apparatus for magnifying displacement of claim 2, wherein the seat further comprises:
    a blocking member convexly disposed on the seat body and connected to the positioning groove, wherein the blocking member is abutted against a front end of the object so as to prevent the object from moving in an extending direction of the positioning groove.

4. The optical measuring apparatus for magnifying displacement of claim 2, wherein,
    the bottom end of the seat body comprises two convex lugs, and each of the two convex lugs comprises a hole; and
    the movable abutting member comprises:
        a shaft disposed through the two holes of the two convex lugs;
        a pivotal portion pivotally connected to the shaft, wherein the shaft is connected between the pivotal portion and the two convex lugs; and a light ball positioning portion integrally connected to the pivotal portion, wherein the dynamic optical sensing element is positioned on the light ball positioning portion.

5. The optical measuring apparatus for magnifying displacement of claim 2, wherein the seat body has a supporting surface, the supporting surface has an arc shape and is corresponding to the positioning groove, and the supporting surface is located between the top end and the bottom end.

6. The optical measuring apparatus for magnifying displacement of claim 1, wherein,
the positioning groove comprises two abutting inclined surfaces, wherein the two abutting inclined surfaces are formed into a V-shape and intersect each other at an intersection, the object is spaced from the intersection by an intersecting distance, the positioning groove has a positioning depth, and the positioning depth is smaller than a sum of the diameter and the intersecting distance.

7. The optical measuring apparatus for magnifying displacement of claim 6, wherein there is an angle between the two abutting inclined surfaces, and the angle is greater than or equal to 80 degrees and smaller than or equal to 100 degrees.

8. An optical measuring system for magnifying displacement to measure a diameter and a length of an object, the optical measuring system for magnifying displacement comprising:
an optical measuring apparatus for magnifying displacement comprising:
a seat comprising a positioning groove;
a movable abutting member pivotally connected to the seat and corresponding to the positioning groove, wherein the object is sandwiched between the movable abutting member and the positioning groove;
a plurality of static optical sensing elements disposed on the seat; and
a dynamic optical sensing element disposed on the movable abutting member, wherein there is an optical sensing distance between the dynamic optical sensing element and one of the static optical sensing elements, the dynamic optical sensing element is moved along an arc path by the movable abutting member so as to change the optical sensing distance, and a change of the optical sensing distance is greater than a change of the diameter of the object;
an optical tracker oriented towards the static optical sensing elements and the dynamic optical sensing element to detect the static optical sensing elements and the dynamic optical sensing element so as to identify the diameter of the object; and
an axial optical measuring device comprising:
a gripping body detachably connected to the object; and
an optical sensor disposed on the gripping body, wherein the optical sensor is detected by the optical tracker to identify the length of the object.

9. The optical measuring system for magnifying displacement of claim 8, wherein the seat further comprises:
a seat body having a top end and a bottom end, wherein the positioning groove is concavely disposed on the seat body, and the bottom end is pivotally connected to the movable abutting member; and
a dynamic reference frame connected to the top end and having a plurality of light ball positioning terminals, wherein the static optical sensing elements are positioned on the light ball positioning terminals, respectively.

10. The optical measuring system for magnifying displacement of claim 9, wherein the seat further comprises:
a blocking member convexly disposed on the seat body and connected to the positioning groove, wherein the blocking member is abutted against a front end of the object so as to prevent the object from moving in an extending direction of the positioning groove.

11. The optical measuring system for magnifying displacement of claim 9, wherein,
the bottom end of the seat body comprises two convex lugs, and each of the two convex lugs comprises a hole; and
the movable abutting member comprises:
a shaft disposed through the two holes of the two convex lugs;
a pivotal portion pivotally connected to the shaft, wherein the shaft is connected between the pivotal portion and the two convex lugs; and
a light ball positioning portion integrally connected to the pivotal portion, wherein the dynamic optical sensing element is positioned on the light ball positioning portion.

12. The optical measuring system for magnifying displacement of claim 9, wherein the seat body has a supporting surface, the supporting surface has an arc shape and is corresponding to the positioning groove, and the supporting surface is located between the top end and the bottom end.

13. The optical measuring system for magnifying displacement of claim 8, wherein,
the positioning groove comprises two abutting inclined surfaces, wherein the two abutting inclined surfaces are formed into a V-shape and intersect each other at an intersection, the object is spaced from the intersection by an intersecting distance, the positioning groove has a positioning depth, and the positioning depth is smaller than a sum of the diameter and the intersecting distance.

14. The optical measuring system for magnifying displacement of claim 13, wherein there is an angle between the two abutting inclined surfaces, and the angle is greater than or equal to 80 degrees and smaller than or equal to 100 degrees.

15. A measuring method applied to the optical measuring apparatus for magnifying displacement of claim 1, the measuring method comprising:
providing an object disposing step, wherein the object disposing step is for disposing the object between the movable abutting member and the positioning groove so as to tightly connect the object between the movable abutting member and the positioning groove; and
providing a radial optical detecting step, wherein the radial optical detecting step is for driving an optical tracker to detect the static optical sensing elements and the dynamic optical sensing element so as to identify the diameter of the object.

16. The measuring method of claim 15, further comprising:
providing an axial optical detecting step, wherein the axial optical detecting step is for driving the optical tracker to detect an optical sensor of an axial optical measuring device so as to identify the length of the object.

* * * * *